US007622532B2

(12) United States Patent
Gadeken et al.

(10) Patent No.: US 7,622,532 B2
(45) Date of Patent: Nov. 24, 2009

(54) SYNTHESIS OF RADIOACTIVE MATERIALS AND COMPOSITIONS OF SAME

(75) Inventors: Larry L. Gadeken, Houston, TX (US); Paul S. Engel, Houston, TX (US); Kenneth S. Laverdure, Lake Jackson, TX (US)

(73) Assignees: William Marsh Rice University, Houston, TX (US); BetaBatt, Inc., Houston, TX (US)

( * ) Notice: Subject to any disclaimer, the term of this patent is extended or adjusted under 35 U.S.C. 154(b) by 216 days.

(21) Appl. No.: 11/676,233

(22) Filed: Feb. 16, 2007

(65) Prior Publication Data

US 2008/0200628 A1  Aug. 21, 2008

(51) Int. Cl.
*C08F 38/00* (2006.01)
*C08F 138/00* (2006.01)
*C08F 238/00* (2006.01)

(52) U.S. Cl. ............... 525/328.1; 525/326.1; 525/338; 525/339; 525/333.7; 136/213; 136/200; 429/5; 252/625; 252/646; 252/644

(58) Field of Classification Search ............... 525/338, 525/339, 328.1, 326.1
See application file for complete search history.

(56) References Cited

U.S. PATENT DOCUMENTS

| | | | |
|---|---|---|---|
| 4,020,003 A * | 4/1977 | Steinberg et al. ............... 588/4 |
| 4,889,660 A | 12/1989 | Jensen et al. |
| 5,100,968 A | 3/1992 | Jensen et al. |
| 5,124,610 A | 6/1992 | Conley et al. |
| 5,606,213 A | 2/1997 | Kherani et al. |
| 5,859,484 A | 1/1999 | Mannik et al. |
| 6,118,204 A | 9/2000 | Brown |
| 6,418,177 B1 | 7/2002 | Stauffer et al. |
| 6,479,920 B1 | 11/2002 | Lal et al. |
| 6,774,531 B1 | 8/2004 | Gadeken |
| 6,949,865 B2 | 9/2005 | Gadeken |
| 2004/0053708 A1 | 3/2004 | Hebert |
| 2004/0267034 A1* | 12/2004 | Anderson et al. ............ 554/141 |
| 2005/0217782 A1* | 10/2005 | Agostini ..................... 152/525 |

FOREIGN PATENT DOCUMENTS

EP   0637037     2/1995
GB    822617    10/1959

OTHER PUBLICATIONS

Mavinkurve et al., High Molecular Weight Poly(4-Trimethylesilyl-1-buten-3-yne), Eur. Polym. J., vol. 33, No. 5, pp. 719-723.*
Helms et al., Dendronized Linear Polymers via "Click Chemistry", J.Am.Chem.Soc. 2004, 126, 15020-15021.*
Mullins et al., Development of Organic Tritium Light Technology at Ontario Hydro, Fusion Technology, Mar. 1992, vol. 21, pp. 213-317.*

Mullins, D.F.; "Development of organic tritium light technology at Ontario hydro"; Fusion Technology, American Nuclear Society, LaGrange Park, Illinois, USA; vol. 21, No. 2; Mar. 1, 1992; pp. 312-317.
"Final Scientific/Technical Report; A Nuclear Microbattery for MEMS Devices: U.S. Department of Energy Award No. DE-FG07-99ID13781," published by James Blanchard et al. of the University of Wisconsin-Madison.
Hahn, S.F., "Hydrogenated Polystyrene: Preparation and Properties," in *Modern Styrenic Polymers*, Scheirs, J.; Priddy, D., Eds. Wiley New York 2003, p. 533.
Helms, B., et al., "Dendronized Linear Polymers via 'Click' Chemistry," J. Am. Chem. Soc., 126, 15020 (2004).
James, B.C., "Homogeneous Hydrogenation," Wiley, New York, 1973 p. 382.
Luttinger, L.B., "Hydride Reducing Agent-Group VIII Metal Compound. A New Catalyst System for the Polymerization of Acetylenes and Related Compounds, I." J. Org. Chem. 1962, 27, 1591.
Ochiai, B.; Tomita, I.; Endo, T.; "Radical Polymerization Behavior of 4-Monosubstituted and 2, 4-Disubstituted Enynes," Macromol. Chem. 2001, 202, 3099.
Steinhart, Martin, et al.; "Nanotubes a la Carte: Wetting of Porous Templates," ChemPhysChem, 4, 1171-6 (2003).
Sun, Wei, et al.; "A Three-Dimensional Porous Silicon p-n Diode for Betavoltaics and Photovoltaics;" Adv. Mater. 2005, 17, 1230-1233.
Wegner, G.; "Polymers with metal-like conductivity—A review of their synthesis, structure, and properties," Anew. Chem. Int. Ed. Engl. 1981, 20, 361.
www.betabatt.com; 128190 Westleigh, Houston, Texas 77077, Ph: 281-450-5449, E-mail: info@betabatt.com; 2005-2007 (1 page).
"Silicon Solution Could Lead to a Truly Long-Life Battery," National Science Foundation; Press Release 05-075; May 10, 2005; University of Rochester; BetaBatt, Inc. (4 pages).
"The 10 Coolest Technologies You've Never Heard of," PCMag.com. (2 pages).

* cited by examiner

*Primary Examiner*—Vasu Jagannathan
*Assistant Examiner*—Robert C Boyle
(74) *Attorney, Agent, or Firm*—Fish & Richardson P.C.; Ross Spencer Garsson

(57) ABSTRACT

The present invention relates generally to synthesis of radioactive material, such as a tritiated polymer, and an apparatus for generating electrical current from the nuclear decay process of a radioactive material. In one embodiment, the invention relates to an energy cell (e.g., a battery) for generating electrical current derived from particle emissions occurring within a radioactive material such as a tritiated polymer) on pore walls of a porous semiconductor. The radioactive material may be introduced into the energy cell by a wetting process.

19 Claims, 7 Drawing Sheets

SYNTHESIS OF RADIOACTIVE MATERIALS AND COMPOSITIONS OF SAME

GOVERNMENT INTERESTS

The present invention was made with support from the National Science Foundation Small Business Innovation Research Phase II Grant No. 0450338.

TECHNICAL FIELD

The present invention relates generally to synthesis of radioactive material, such as a tritiated polymer, and an apparatus for generating electrical current from the nuclear decay process of a radioactive material. In one embodiment, the invention relates to an energy cell (e.g. a battery) for generating electrical current derived from particle emissions occurring within a radioactive material such as a tritiated polymer) on pore walls of a porous semiconductor. The radioactive material may be introduced into the energy cell by a wetting process.

BACKGROUND

Electrical current directly derived from a nuclear decay process is frequently referred to as an "alpha-voltaic" or "beta-voltaic" effect, depending on whether the charged particle emitted by a particular nucleus is an alpha particle or a beta particle, respectively. Previously, a major drawback when attempting to use energy derived from a nuclear decay series to power devices in remote locations has been an inefficiency of the energy conversion process.

Tritium-containing polymers are described in U.S. Patent Application Publication No. 20050217782 to Agostini, U.S. Patent Application Publication No. 20040053708 to Hebert; U.S. Pat. Nos. 5,100,968 and 4,889,660 to Jensen et al.; U.S. Pat. No. 4,020,003 to Steinberg et al.; U.S. Pat. No. 5,124,610 to Conley et al.; U.S. Pat. No. 6,418,177 to Stauffer et al. A description of efforts to exploit the nuclear decay process of a radioactive material is found in "Final Scientific/Technical Report: A Nuclear Microbattery for MEMS Devices; U.S. Department of Energy Award No. DE-FG07-991D13781," published by James Blanchard et al. of the University of Wisconsin-Madison. Other references to nuclear batteries include U.S. Pat. No. 6,479,920 to Lal et al.; U.S. Pat. No. 6,118,204 to Brown; U.S. Pat. No. 5,859,484 to Mannik et al.; U.S. Pat. No. 5,606,213 to Kherani et al.; and U.S. Pat. Nos. 6,774,531 and 6,949,865 to Gadeken. All of the foregoing are incorporated herein by reference.

SUMMARY

This invention relates to radioactive material including carbon and tritium and a beta-voltaic cell that includes the same. In general, in one aspect, the invention features a process including selecting an organic material and tritiating the organic material to yield a tritiated material. The tritiated material has a ratio of tritium atoms to carbon atoms of at least about 1:1. The step of tritiating of the material includes addition and/or substitution methods.

Implementations of the invention can include one or more of the following features. The organic material can be a polymer (with the resulting tritiated material being a tritiated polymers). The polymer can be a poly(vinylacetylene), such as TMS poly(vinylacetylene). The amount of tritium in the tritiated material can be at least about 20 wt %. The tritiated polymer can be $[C_4H_3T_5]_n$. The tritiated polymer can be tritiated poly(1-ethylethylene). The tritiated polymer can be saturated. The step of tritiating the polymer can include catalytic tritium addition. The polymer can have a carbon-carbon triple bond (or a carbon-carbon double bond) in at least one monomer unit of the polymer, and the step of tritiating the polymer can further include addition of the tritium in the form of tritium gas to the carbon-carbon triple (or double) bond. The step of tritiating the polymer can include $T_2O$ hydrolysis. The ratio of tritium atoms to carbon atoms in the tritiated polymer can be at least about 1.25:1, or more specifically at least about 1.5:1, or even more specifically at least about 2:1. The polymer can be synthesized from two or more compounds, one of which includes vinyl bromide. The synthesizing of the polymer can include reacting vinyl bromide with trimethylsilyacetylene ((TMS) acetylene) and, optionally, the vinyl bromide can be tritiated before the synthesizing of the polymer. The polymer can include some tritium atoms before further tritiating the polymer utilizing addition and/or substitution methods.

In another aspect, the invention features a process including reacting vinyl bromide with trimethylsilyacetylene ((TMS) acetylene) in the presence of a palladium catalyst to form. TMS protected vinylacetylene; polymerizing the TMS protected vinylacetylene to generate TMS PVacet; hydrolyzing the TMS PVacet with $T_2O$ to form PVacet-T; and adding tritium to the PVacet-T to yield tritiated poly(1-ethylethylene).

In another aspect, the invention features a saturated polymer comprising carbon and tritium. The saturated polymer has a ratio of tritium atoms to carbon atoms of at least about 1:1.

Implementations of the invention can include one or more of the following features. The saturated polymer can be tritiated poly(1-ethylethylene). The saturated polymer can have at least one monomer unit that includes at least 5 tritium atoms.

In another aspect, the invention features a method of making a beta-voltaic cell that includes tritiating an organic material to yield a tritiated material and at least partially wetting at least one pore of a porous semiconductor with a liquid including the tritiated material. The tritiated material has a ratio of tritium atoms to carbon atoms of at least about 1:1. The tritiating of the organic material includes an addition and/or substitution method. The pore has disposed within it a first portion of a junction region.

Implementations of the invention can include one or more of the following features. The organic material can be a polymer (with the resulting tritiated material being a tritiated polymer). The step of wetting may include melt-wetting and/or solution-wetting, to form a film on a solid surface (for instance, pore walls of a porous semiconductor). The film may be a mesoscopic film. The porous semiconductor can include silicon, which can be macroporous silicon. The opening of the pore can have a diameter between about 1 nm and about 500 μm. The porous semiconductor can include doped silicon. The tritiated polymer can include tritiated poly(1-ethylethylene). The porous semiconductor can be heated and/or cooled during the process. During the wetting step, a layer of thickness of about 30 nm to about 50 nm can be formed on the walls of at least the pore in the porous semiconductor.

In another aspect, the invention features an apparatus for generating electrical current from a nuclear decay process of a radioactive material. The apparatus includes a porous semiconductor wafer. At least one pore of the porous semiconductor wafer is at least partially coated with the radioactive material. The radioactive material includes a tritiated material having a ratio of tritium atoms to carbon atoms of at least about 1:1. The pore of the porous semiconductor wafer includes a first portion of a junction region.

Implementations of the invention can include one or more of the following features. The organic material can be a polymer (with the resulting tritiated material being a tritiated polymer). At least one of the porous semiconductor wafers can include silicon, which can be macroporous silicon. The first portion of the junction region can be disposed at a declination angle of greater than about 55° relative to a second portion of said junction. The tritiated polymer can include tritiated poly(1-ethylethylene). The tritiated polymer can include a saturated polymer. The pore can have an aspect ratio of at least about 20:1.

In further embodiments, features from specific embodiments may be combined with features from other embodiments. For example, features from one embodiment may be combined with features from any of the other embodiments. In further embodiments, additional features may be added to the specific embodiments described herein.

BRIEF DESCRIPTION OF THE DRAWINGS

Advantages of the present invention will become apparent to those skilled in the art with the benefit of the following detailed description and upon reference to the accompanying drawings in which.

Figure 1:
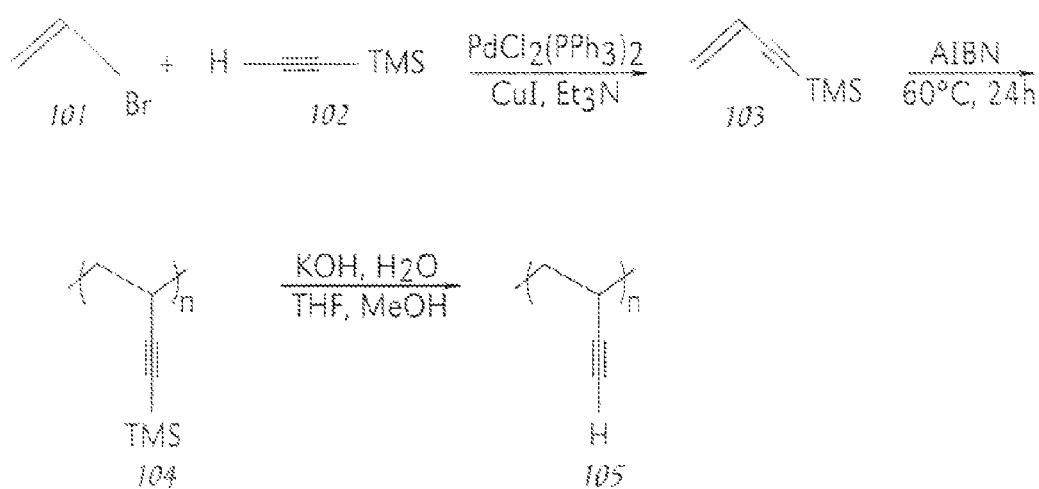
FIG. 1 depicts a process for the preparation of poly(vinylacetylene) known in the prior art.

While the invention may be susceptible to various modifications and alternative forms, specific embodiments thereof are shown by way of example in the drawings and will herein be described in detail. The drawings may not be to scale. It should be understood, however, that the drawings and detailed description thereto are not intended to limit the invention to the particular form disclosed, but to the contrary, the intention is to cover all modifications, equivalents, and alternatives falling within the spirit and scope of the present invention as defined by the appended claims.

DETAILED DESCRIPTION

The following terms shall have the definitions given below when used in either lower case or with capitalizations in this specification:

"Addition" is defined as a chemical reaction in which two or more molecules, one of which includes at least one carbon-carbon double bond and/or at least one carbon-carbon triple bond, combine to form a larger molecule.

"Exchange" is defined as a chemical reaction in which atoms of the same element in two different molecules or in two different positions in the same molecule exchange places. Exchange reactions include reactions in which one isotope of an element is replaced by a different isotope of the same element.

"Liquid polymer" refers to any substance in the liquid state that includes a polymer. Liquid polymers include, but are not limited to, a polymer melt or a solubilized polymer.

"Polymer" and "polymeric material" refer to a substance including one or more of various types of polymers (e.g., block copolymer, graft copolymer, star polymer, random copolymer, etc.)

"Saturated polymer" refers to a polymer containing no multiple (i.e., double or triple) bonds.

"Substitution" is generally defined as a chemical reaction in which one element or group is replaced by a different element or group as a result of a chemical reaction.

"Tritiating" a substance (e.g., a carbon-containing molecule, monomer, polymer, etc.) refers to incorporating tritium into the substance through the formation of one or more carbon-tritium covalent bonds.

The present invention relates to the preparation of radioactive material for beta-voltaic cells, which includes the preparation of a radioactive material, such as tritiated organic material or tritiated polymer, with a high energy density through an efficient process that achieves high utilization of the radioactive material and produces low amounts of contaminated waste products. With a radioactive source (e.g., tritium) incorporated into an organic structure (for instance, a polymer), leaking or leaching of radioactive material into the environment can be inhibited.

Organic materials suitable for tritiation include, but are not limited to, monomers, oligomers, and polymers. In some embodiments, monomers may be tritiated, and the tritiated monomers may be used to form tritiated polymers. The tritiated polymers may be further tritiated. In other embodiments, a non-radioactive polymer may be tritiated. The tritiated polymer may then be further tritiated. Examples of organic material that may be tritiated include, for instance, vinyl bromide and poly(vinylacetylene). Vinyl bromide and poly(vinylacetylene) are used herein as examples of organic materials suitable for tritiation. Other organic materials known in the art may also be tritiated to form radioactive material suitable for generation of electrical current from beta-voltaic cells.

Mavinkurve, et al., "High molecular weight poly(4-trimethylsilyl-1-buten-3-yne)," *European Polymer Journal*, 1997 33(5):719-723, describes synthesis of poly-(vinylacetylene) selective polymerization of 4-trimethyl-1-buten-3-yne through the vinyl group, followed by cleavage of the protective trimethylsilyl group. At low temperatures, the monomer undergoes self-initiated polymerization leading to an ultra-high molecular weight polymer. Matnishyan et al., "Characteristic Features of the Polymerisation of Acetylene and Its Derivatives," *Russ. Chem. Rev.*, 1983, 52(8):751-756, describes methods of preparation of high-molecular-weight polymers.

Work by Helms et al., ("Dendronized Linear Polymers via Click Chemistry" *J. Am. Chem. Soc.* 2004, 126, 15020-15021, which is incorporated by reference herein) describes a solution phase procedure to produce poly(vinylacetylene). The synthesis of poly(vinylacetylene) (PVacet) described by Helms et al. is depicted in FIG. 1. As shown in FIG. 1, vinyl bromide 101 is reacted with trimethylsilylacetylene ((TMS) acetylene 102 in the presence of a palladium catalyst ($PdCl_2$ ($PPh_3$)$_2$), copper iodide, and triethylamine to form TMS protected vinylacetylene (TMS-1-buten-3-yne) 103 in a Sonogashira reaction. Bulk polymerization initiated with azoisobutyronitrile (AIBN) at 60° C. generates TMS PVacet 104. Hydrolysis of the TMS moiety in an excess of KOH and MeOH yields PVacet 105.

Figure 2:
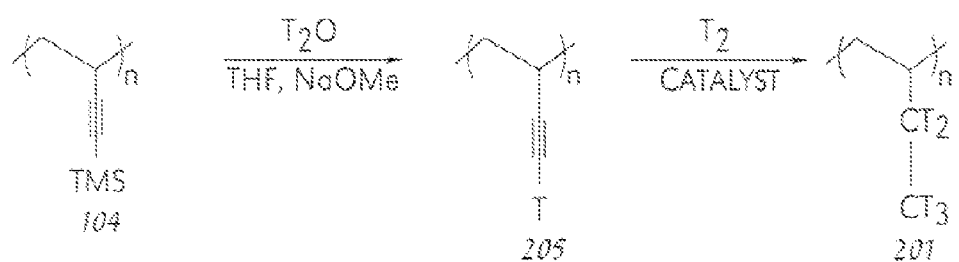
FIG. 2 depicts the preparation of tritiated poly(1-ethylethylene) from TMS poly(vinylacetylene).

For complete tritiation, however, exchangeable hydrogens must be substantially absent from the reaction mixture. Departing from FIG. 1, a tritium atom may be substituted for the TMS moiety by $T_2O$ hydrolysis of the TMS moiety in TMS PVacet 104 in the presence of NaOMe and THF to form PVacet-T 205, as depicted in FIG. 2. In an example, 218 mg (4.03 mmol) anhydrous NaOMe and 88.7 mg (4.03 mmol) of $T_2O$ are added to 500 mg of polytrimethylsilylvinylacetylene (4.03 mmol of TMS groups) dissolved in 20 mL THF. After stirring at 50° C. for 48 hours, the solvent mixture is removed under vacuum to yield PVacet-T 205. In some embodiments, an excess of NaOMe and $T_2O$ may be used.

Catalytic tritium addition of four tritium atoms to each carbon-carbon triple bond of PVacet-T 205 yields tritiated poly(1-ethylethylene) $[C_4H_3T_5]_n$ 201. In some embodiments, catalytic tritium addition may be achieved with $T_2$ in the presence of Wilkinson's chlorotri(triphenylphosphine) rhodium. In other embodiments the catalyst may be metallocene/butyllithium, as described by Tsiang, et al., "Hydrogenation of polystyrene-b-polybutadiene-b-polystyrene block copolymers using a metallocene/n-butyllithium catalyst; the role of n-butyllithium," *"J. Appl. Polym. Sci.* 1999, 72(14):1807-1815. In still further embodiments, heterogeneous catalysts including, but not limited to, Pd/C or Pt/C may be used at elevated pressures and/or temperatures.

Tritiated poly(1-ethylethylene) $[C_4H_3T_5]_n$ 201 may be completely saturated. The fully saturated, tritiated polymer includes about 23 wt % tritium, with a ratio of tritium atoms to carbon atoms in each monomer unit of 1.25:1, and a molecular weight ranging from about 20,000 to about 200,000. Radioactivity of $[C_4H_3T_5]_n$ generally will be in a range from about 1,000 Ci/g to about 5,000 Ci/g.

The synthesis depicted in FIG. 2 involves introduction of tritium at the final stages of the synthesis (e.g., tritiating a polymer rather than precursor monomer units), thereby limiting handling of tritium-containing compounds. The substitution and addition reactions depicted in FIG. 2 to form PVacet-T 205 and $[C_4H_3T_5]_n$ 201, respectively, allow efficient synthesis while limiting the production of contaminated (e.g., radioactive) waste. The scheme in FIG. 2 is an example of a method to produce a saturated, tritiated polymer with substitution and addition reactions to cleanly and efficiently incorporate or introduce tritium into a polymer. The scheme in FIG. 2 does not include an exchange reaction between protium and tritium.

In alternative embodiments of the invention, the processes shown in FIGS. 1 and 2 can be modified such that the pendant group in each monomer unit of the radioactive polymer is a longer carbon chain. For instance, when the pendant group in each monomer unit is a butyl group (instead of an ethyl group, as in poly(1-ethylethylene)), the resulting radioactive polymer is of the form $[C_4H_3T_5]_n$, with a ratio of tritium atoms to carbon atoms in each monomer unit of 1.5:1. The ratio will approach about 2:1 as the pendant group becomes longer.

In another alternative embodiment of the invention, the tritium:carbon ratio may be increased by deprotecting TMS poly(vinylacetylene) with fluoride in the presence of $C_2T_5I$, resulting in monomeric units with the formula $C_6H_3T_5$ before addition of $T_2$ across the triple bond. Full tritiation would then yield $C_6H_3T_9$, with a tritium:carbon ratio of 1.5:1.

In still alternative embodiment of the invention, the processes shown in FIGS. 1 and 2 can be modified to begin with tritiated vinyl bromide ($C_2T_3Br$) rather than vinyl bromide ($C_2H_3Br$) 101. As such, after polymerization, substitution, and addition, the resultant tritiated poly(1-ethylethylene) is $[C_4T_8]_n$, with a ratio of tritium atoms to carbon atoms in each monomer unit of 2:1.

A radioactive material in a liquid state may be used to wet one or more pores of a porous semiconductor to provide a source of beta particles for a beta-voltaic cell. As used herein, "wetting" is generally defined as a process by which an interface between a solid and a gas is replaced by an interface between the same solid and a liquid. Steinhart et al. describe wetting of porous templates to form nanotubes in "Nanotubes a la Carte: Wetting of Porous Templates" *CHEMPHYSCHEM* 2003, 4, 1171-1176, which is incorporated by reference herein.

Wetting behaviour is described by the spreading parameter S:

$$S = \gamma_{sv} - \gamma_{sl} - \gamma_{lv},$$

in which $\gamma_{sv}$ is the solid-vapor interfacial tension, $\gamma_{sl}$ is the solid-liquid interfacial tension, and $\gamma_{lv}$ is the liquid-vapor interfacial tension. When (a) the solid is a porous semiconductor, (b) the liquid is a liquid form of a radioactive material (such as a radioactive polymer), and (c) the vapor includes air or any combination of gases including inert gases (e.g., nitrogen, argon), adhesive forces between the polymer liquid and the semiconductor exceed the cohesive forces with the polymer liquid, thereby allowing the polymer liquid to spread on the porous semiconductor.

Wetting may involve the formation of a precursor film as the liquid polymer spreads on the porous substrate. A microscopic precursor film may form near an edge of a macroscopic liquid polymer droplet. The precursor film may spread on the order of millimeters, with a thickness ranging of a few tens of nanometers.

Figure 3:
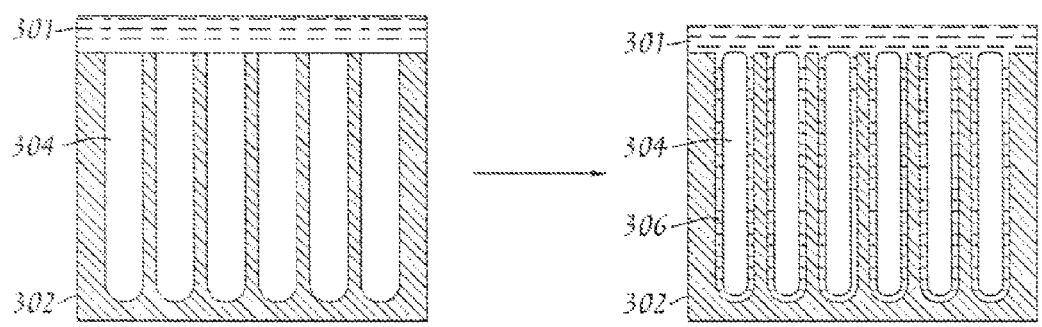
FIG. 3 is a sectional view of an embodiment of a process of wetting pores in a porous semiconductor with radioactive material.

FIG. 3 is a sectional view of an embodiment of the process of wetting pores in a porous semiconductor (e.g., a silicon wafer) with liquid polymer. As depicted in FIG. 3, liquid polymer 301 may be a contact with a porous surface of porous semiconductor 302. Liquid polymer 301 may have a lower surface energy than porous semiconductor 302, allowing the liquid polymer to at least partially wet the surface of the porous semiconductor, including walls of pores 304 in the porous semiconductor. Cohesive forces necessary to completely fill pores 304 of porous semiconductor 302 may be lacking, such that the pores may be wetted, but not substantially filled, with liquid polymer 301, as depicted in FIG. 3. Pore walls in porous semiconductor 302 may be at least partially covered with layer 306. In some embodiments, layer 306 may be a film (e.g., a mesoscopic film).

As used herein, "mesoscopic" film refers to a film with a thickness characterized by properties intermediate between the properties of bulk matter and individual atoms or molecules. As used herein, "coat" generally refers to a layer or film, or forming such layer or film, on a pore wall of a porous semiconductor. The coat or coating may be in a liquid or solid state. The coat, layer, or film may have a thickness ranging from about 1 nm to about 100 nm. As used herein, "wetting" generally refers to forming a layer of liquid on a solid surface, including pore walls of a porous solid. In some embodiments, wetting of pore walls of a porous semiconductor by a liquid radioactive material (such as a radioactive polymer) may occur over a period of time of 1-100 seconds.

Pores of a porous semiconductor may be wet with a polymer liquid by methods including, but not limiting to, solution-wetting and melt-wetting. Solution-wetting may include contacting a polymer melt of a liquid containing one or more polymers and one or more additional components with a porous surface of a semiconductor. For instance, poly(1-ethylethylene) may be dissolved in any suitable solvent known in the art including, but not limited to, acetone, tetrahydrofuran, chloroform, toluene, or a mixture thereof to form a liquid radioactive polymer. A liquid polymer applied to (e.g., brought in contact with a porous surface of) a porous semiconductor may be homogeneous. The morphology of a polymeric coating of a pore wall may be selectively controlled through processes including, but not limited to, thermal quenching or solvent evaporation to induce phase separation along with phase ripening.

Melt-wetting may include placing or pressing polymer powders or pellets on a porous surface of a semiconductor that has been heated to a temperature that exceeds the glass transition temperature of an amorphous polymer or the melting point of a partially crystalline polymer. In some embodiments, wetting of pore walls of a porous semiconductor by a liquid polymer may occur over a period of time of 1-100 seconds. Cooling of the polymer melt (e.g., cooling the porous semiconductor wetted by the polymer melt) may result in a polymeric layer coupled to one or more pore walls. As used herein, "coupled" generally refers to joined or linked together, with or without an intervening substance or material. A polymeric layer may be removably or permanently coupled to one or more pore walls. The method of wetting the pore walls, including heating and/or cooling the porous semiconductor or substrate, may be chosen to achieve a desired thickness and/or morphology of the resulting polymeric layer coupled to the pore walls.

Sun, et al., "A Three-Dimensional Porous Silicon p-n Diode for Betavolaics and Photovolaics," *Adv. Mat.* 2005, 17, 1230-1233 (which is incorporated by reference herein), describes a three-dimensional diode constructed on porous silicon, which consists of a network of pores formed by electrochemical anodization of silicon substrates. Porous silicon is classified according to pore size as microporous ($\leq 2$ nm), mesoporous (20-50 nm), or macroporous ($\geq 50$ nm). As used herein, "pore size" and "pore diameter" generally refer to a diameter of an opening of the pore (e.g., a "throat" of the pore).

In some embodiments, appropriate materials having pore sizes within any of the aforementioned size ranges (e.g., nanometer-scale structures, such as carbon nanotubes) may be used. In other embodiments, a quantum wire of radioactive atoms strung in a polymer chain may be inserted into a pore with a slightly larger diameter than the chain.

In some embodiments of the invention, a silicon formation is used in which an individual pore diameter is between about 1 nm and about 500 μm. In other embodiments, pores having a diameter between about 1 nm and about 100 μm are formed. In still other embodiments, pores having a diameter of between about 1 nm and about 70 μm are formed.

In some embodiments, the pore depth extends through the entire thickness of a semiconductor wafer. In such embodiments, the junction regions of the pores are interconnected by a variety of means that will occur to those of skill in the art (e.g., exterior wire-bond connection, metalization deposits on the wafer, and/or conductive layers within the wafer itself).

In a further embodiment, channels, are formed in the wafer, wherein a width of the channels is on the order of a micron. For instance, in embodiments of the invention, channels having a diameter between about 1 nm and about 500 μm may be formed. In other embodiments, channels having a diameter between about 1 μm and about 100 μm may be formed. In some embodiments, channels having a diameter of about 70 μm may be formed. The channels may be formed as a series or array of channels.

Figure 4:
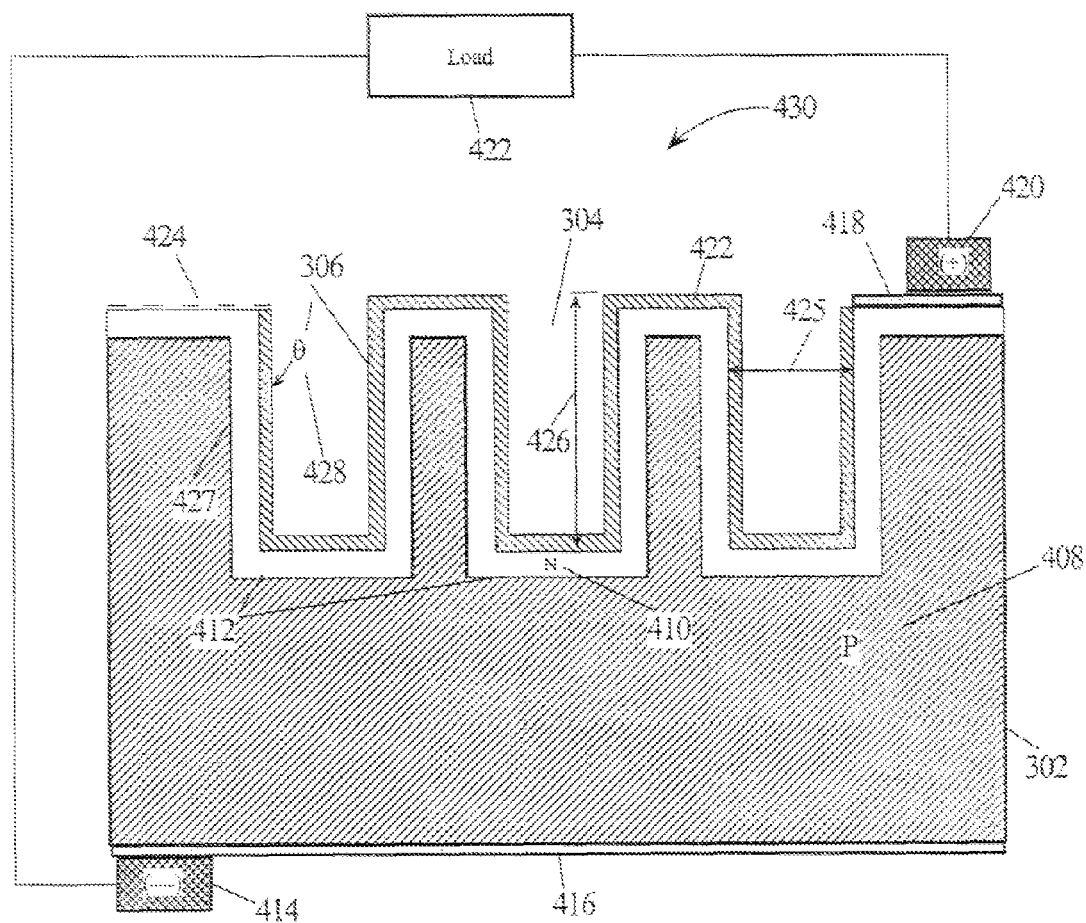
FIG. 4 is a schematic representation of an embodiment of a beta-voltaic cell.

Referring now to FIG. 4, an embodiment of diode structure 430 is seen in which porous semiconductor 302 has been doped to provide p-type region 408, n-type region 410, and junction region 412. In some embodiments, porous semiconductor 302 may include silicon. First contact 414 connects p-type region 408 to a first side of load 423 via low-resistivity contact region 416 (e.g., a metal, for instance, aluminum). Second contact 420 connects n-type region 410 via low-resistivity contact surface region 418 (e.g., a metal deposit, for instance, gold) thereby permitting a current transport path for charges liberated by energetic decay electron energy absorption in n-type region 410 to reach second contact 420, such that n-type region 410 is in electrical communication with another side of load 423.

Radioactive material 422 is disposed in layer 306 coupled to pores 304. Each decay event in radioactive material 422 generates an energetic beta particle that may enter n-type region 410 which has an electric field across junction 412 caused by the contact potential between p-type region 408 and n-type region 410. In this embodiment, the emitted beta particle enters n-type region 410 and creates positive (holes) and negative (electrons) charges within n-type region 410 that separate under the influence of the electric field in junction 412. One charged species migrates towards junction region 412 and then to low-resistivity contact region 416, while an oppositely charged species migrates toward a contact surface region (e.g., 416 or 418). In this manner, a current flow through load 423 is induced via first contact 414 and second contact 420.

The maximum travel distance of the most energetic tritium beta particle in silicon is about 4.33 μm; and, in an embodiment employing a silicon wafer and tritiated organic material (tritiated polymer), junction region 412 may be created near a boundary of p-type region 408 and n-type region 410 at a depth just past 4.33 μm. Disposition of the junction region at a depth greater than the maximum travel distance of the beta particle provides a nearly 100% chance that all of the charge generated when a beta particle travels through n-type region 410 will be collected, and therefore contribute to the total generated current.

Pores 304, in various embodiments, have diameter 425 of significantly less than the "mean free path" of the decay particle of the radioactive material disposed in the pore for the purpose of increasing the probability that a decay event will cause current to be generated. In further embodiments, pores 304 have length 426, with a length-to-diameter aspect ratio of greater than about 20:1. In a still further embodiment, pores 304 have an aspect ratio of greater than about 30:1, again for the purpose of increasing the probability that a decay event will result in a particle entering the semiconductor and generating current. In still further embodiments (for instance, see FIG. 4), the walls of pores 304, and consequently the exemplary junction region 427 of junction 412 formed between p-type region 408 and n-type region 410, have a declination angle θ of greater than about 55° (measured relative to surface plane 424 of the semiconductor surface in which they are formed). In the embodiment illustrated in FIG. 4, for instance, the walls of pores 304, and thus, the exemplary junction regions 427, have a declination angle θ 428 of about 90° measured relative to surface plane 424 of the semiconductor in which they are formed. When the radioactive material is disposed in a long, narrow volume in a semiconductor, there is a much greater probability that a beta particle produced by a decay event will enter junction region 412 and induce a current flow. Disposing the radioactive material in a manner such that a decay particle is produced a significant fraction of a mean free path or further from the nearest energy conversion function causes a much lower current density to result from any particular volume of a semiconductor.

It should be noted that the current of a particular device is related, at least in part, to the surface area of the junction region 412 available to collect electrons quickly after the decay event. The greater the area of junction region 412 provided in a particular volume of radioactive material, the greater the induced current. The voltage of a particular device depends, at least in part, on the voltage of junction region 412. For silicon-material junction regions, that voltage is about 0.7 volts. For other junction regions, whether derived from different semiconductor materials (e.g., germanium, gallium-arsenide, etc.) and/or other structural configurations (e.g., plated metal disposed over selected portions of a semiconductor material), the voltage is different.

The diode structure 430 in FIG. 4 effectively parallels a number of pn-junctions, each formed in the pores 304 and to some extent over the surface of p-type region 408. The structure of FIG. 4 would be fabricated over an area of p-type region 408, creating a diode structure 430. To configure a diode structure that generates more current or voltage than is possible with a single diode structure 430, requires the parallel and/or series combinations of the diode structures 430.

Figure 5A:
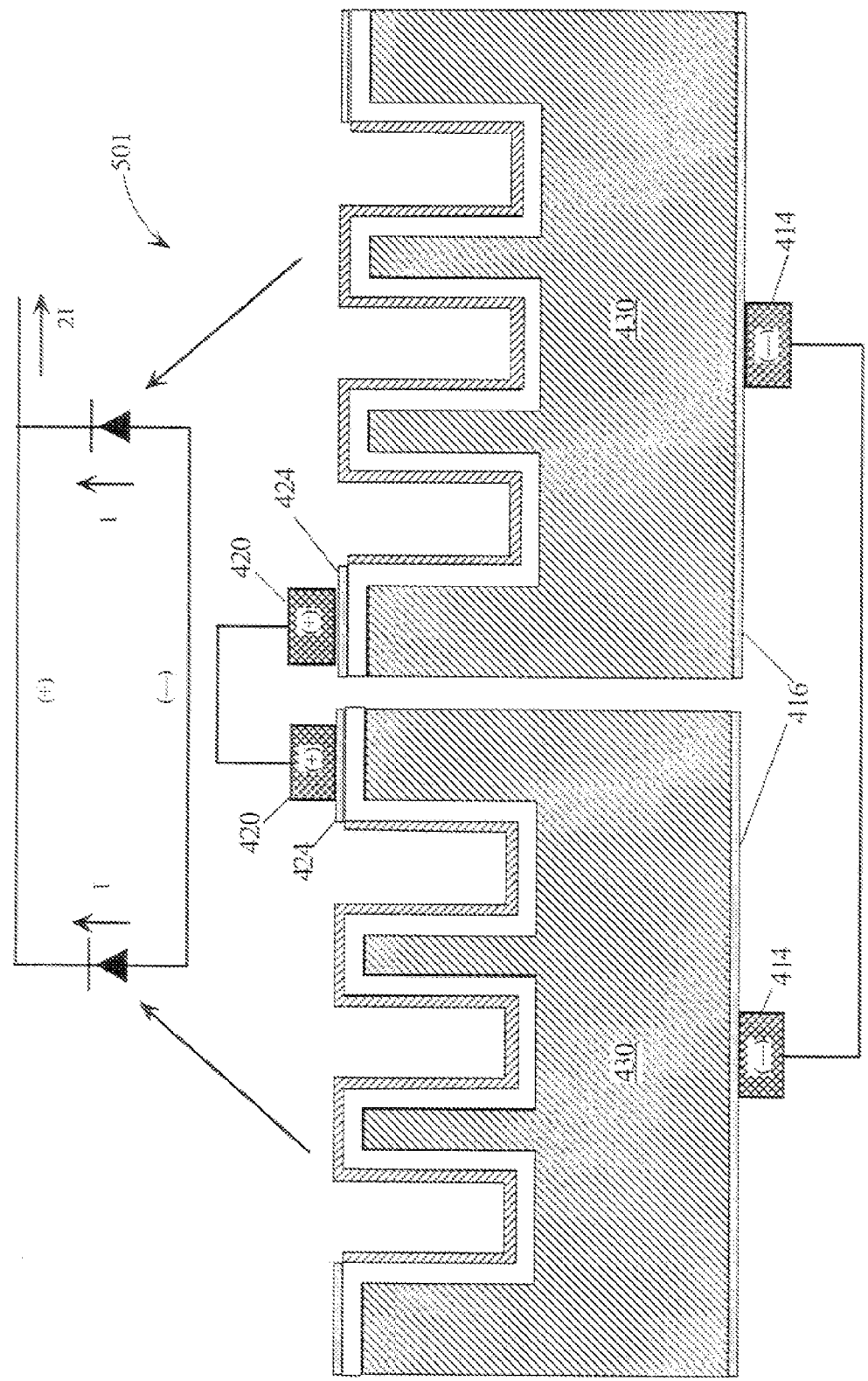
FIG. 5A is a schematic representation of another embodiment of a beta-voltaic cell.

FIG. 5A depicts a sectional view of a parallel combination 501 of two diode structures 430 for generating substantially twice the current possible with a single diode structure 430. The detail of the diode structures 430 are shown in FIG. 4 and are not repeated relative to FIG. 5A. Contacts 420 are coupled and connect to the n-type regions 410 via low resistivity contact region 418 to form the positive terminal of parallel combination 501. Likewise, contacts 414 are coupled and connect to the p-type regions 408 via low resistivity contact region 416. Other embodiments may electrically couple more than two diode structures 430 in parallel using various mechanical configurations to realize desired form factors.

Figure 5B:
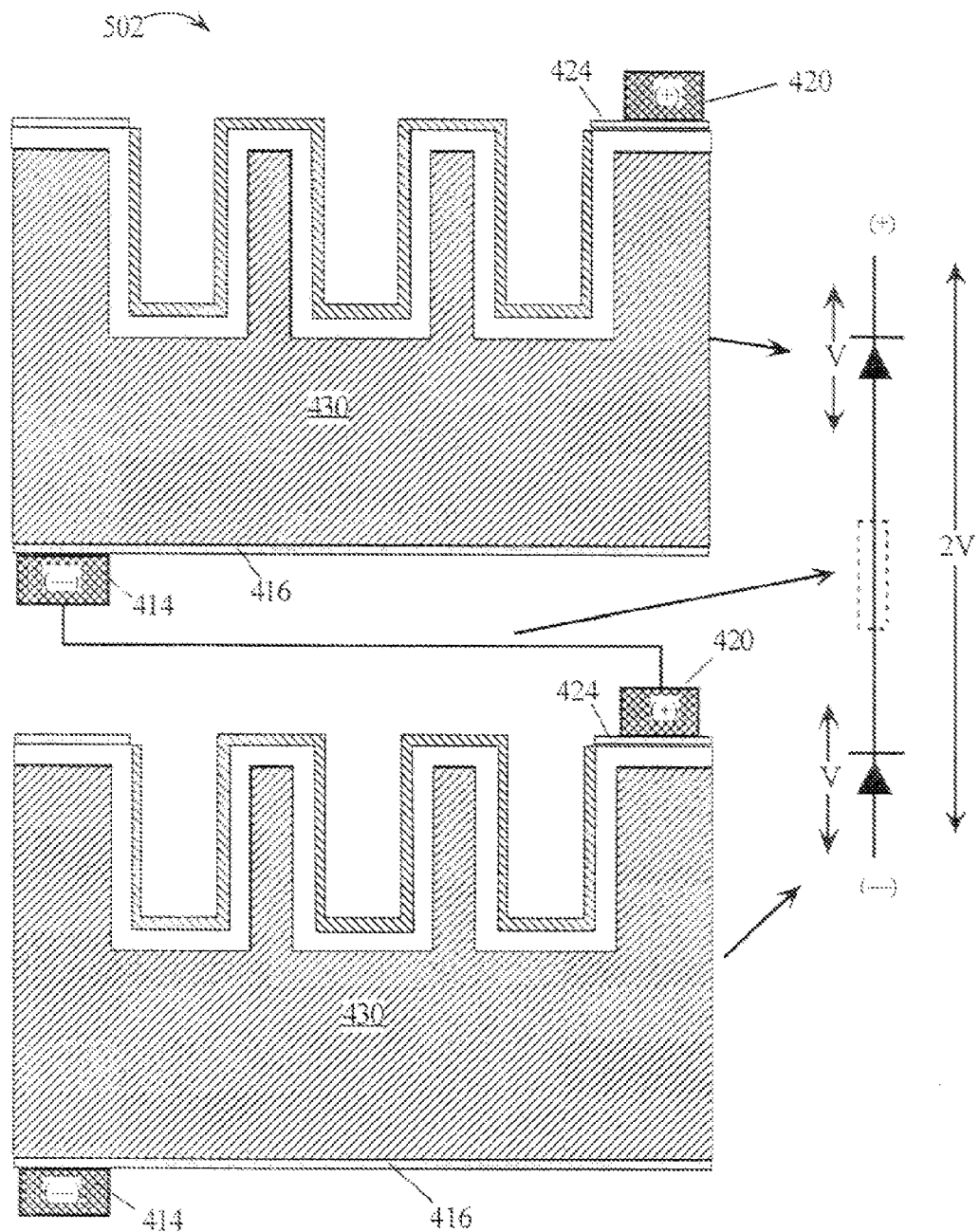
FIG. 5B is a schematic representation of another embodiment of a beta-voltaic cell.

FIG. 5B depicts a sectional view of a series combination 502 of two diode structures 430 for generating substantially twice the voltage possible with a single diode structure 430. The detail of the diode structures 430 are shown in FIG. 4 and are not repeated relative to FIG. 5B. In this embodiment, one contact 420 (coupled to the n-type region) in one diode structure 430 is coupled to one contact 414 (coupled to the p-type region) in the other diode structure 430. The other contact 420 and the other contract 414 become the output terminals of the series combination 502. Other embodiments may electrically couple more than two diode structures 430 in series using various mechanical configurations to realize desired form factors. While not shown, it is also possible to fabricate series/parallel combinations of the macro diode structures 430 to generate desired output voltages with desired current supply capabilities. These structures are considered within the scope of the present invention.

Diode structures 430 may include one or more (e.g., a plurality of) etched channels or pores 304. Channels or pores 304 may have doped junction regions 412 formed on the inner surfaces of said channels or pores. Radioactive material (radioactive polymer) 422 may be positioned (e.g., confined) within diode structure 430. For instance, layer 306 may be coupled to or deposited on one or more pore walls. In a further embodiment, radioactive material (radioactive polymer) 422 may include a non-radioactive material that may be converted into an appropriate radioactive species which thereafter decays when irradiated or otherwise excited by appropriate means.

In an embodiment, existing semiconductor fabrication methods are used to form porous silicon wafers having a plurality of etched pores or channels. See, for example, U.S. Pat. No. 6,204,087 B1 to Parker et al. U.S. Pat. No. 5,529,950 to Hoenlein et al.; and U.S. Pat. No. 5,997,713 to Beetz, Jr. et al., all of which are incorporated herein by reference. Generally, a pore or channel pattern is deposited onto the wafer. Masking is performed using, for instance, photolithography and/or photo-masking techniques. Exposed portions of the wafer are etched (for instance, by exposure to a chemical solution, or gas plasma discharge) to remove areas of the wafer that were not protected during the masking stage.

In an embodiment of the present invention, inner surfaces of the etched pores are substantially curved in shape, for instance, cylindrical or conical. In an alternative embodiment, a series of very narrow channels having dimensions of a few microns are etched. In a still further embodiment, the etched pores and/or channels are formed in the wafer in positions that are substantially equidistant from one another. In further embodiments, pores and/or channels etched into the wafer are substantially the same shape, although, in other embodiments, some of the pores and/or channels have differing shapes.

The electrical properties of the etched area may then be altered by the addition of doping materials. In an embodiment of the invention, known doping methods are used to alter the electrical properties of the etched pores or channels. See, for example, "Deep Diffusion Doping of Macroporous Silicon," published by E. V. Astrova et al. of the A. F. Ioffe Physico-Technical Institute, Russian Academy of Sciences, St. Petersburg in December 1999 and March 2000, each of which is incorporated herein by reference. In some embodiments, the wafer is doped by applying atoms of other elements to the etched areas. In some embodiments, the added elements have at least one electron more than silicon and are called p-type (e.g., boron). In further embodiments, the added elements have at least one electron less than silicon and are called n-type (e.g., phosphorus).

Accordingly to a further embodiment, preparation of appropriate diode structures 430 (see FIG. 4) is performed using known doping techniques. In an embodiments of the invention, channels or pores 304 are etched (e.g., in an array) into the bodies of diode structures 430, and then doped to form a plurality of junction regions 412 on the inner wall surfaces of channels or pores 304. Radioactive material (radioactive polymer) 422 may be introduced into channels or pores 304 through a process including, but not limited to, wetting with radioactive material. The diode structures 430 may be assembled as desired.

As mentioned supra, in some embodiments in which the radioactive material includes tritium, the emitted charged particles are beta electrons. Beta electrons have a relatively low penetrating power. Accordingly, in some embodiments, a housing may be formed from a thin sheet of metallic foil, which inhibits penetration of energetic particles emitted during the decay process. Thus, the possibility of radioactive energy escaping from the package is reduced. Use of tritiated material (for instance, tritiated polymer) reduces the need for precautions related to inadvertent release of tritium from the cell into environment.

Figure 6A:
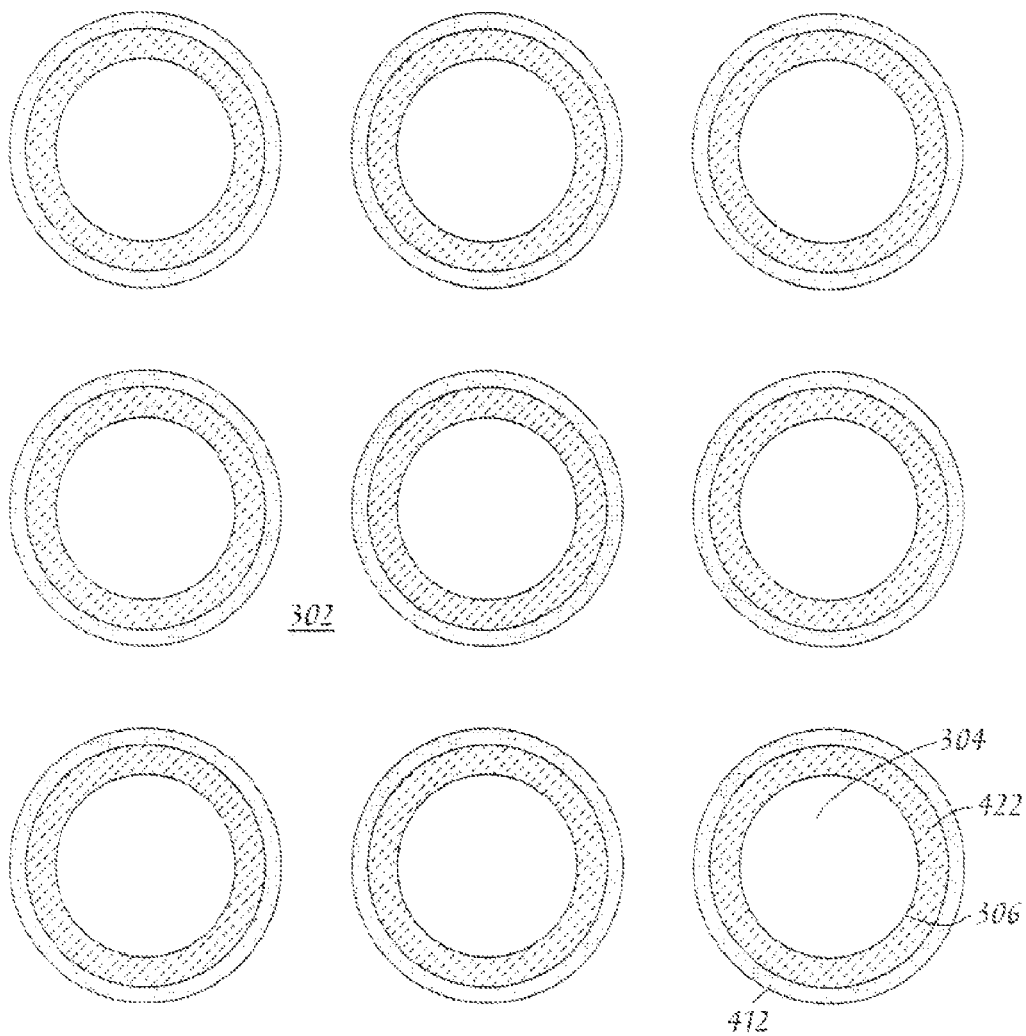
FIG. 6A is a sectional view of an embodiment of a pore array in a porous semiconductor.
Figure 6B:
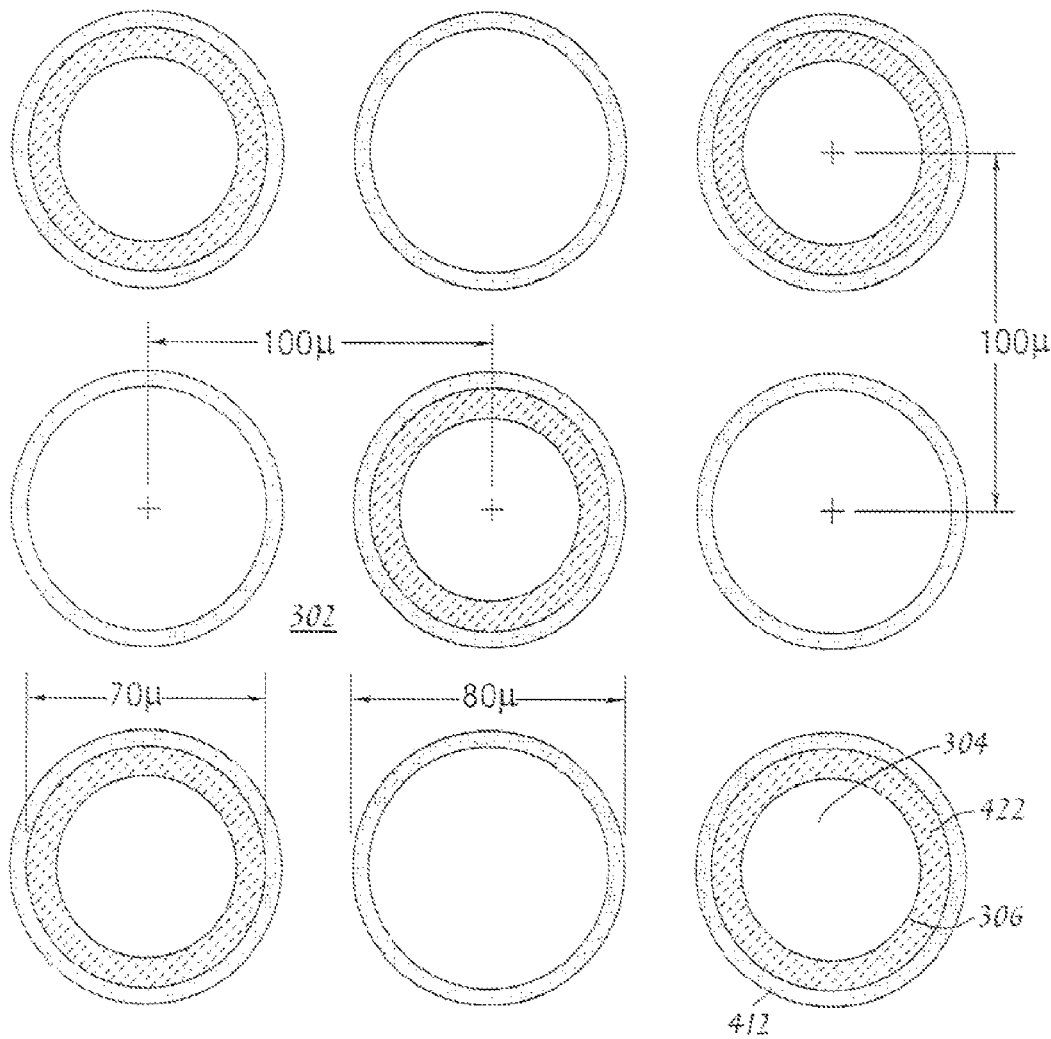
FIG. 6B is a sectional view of another embodiment of a pore array in a porous semiconductor.

In further embodiments, FIG. 6A and FIG. 6B show a pore array formed within a diode structure for generating electrical current from the decay process of radioactive material (radioactive polymer). As seen, a 3×3 array of circles represents a sectional view of channels or pores 304 etched into porous semiconductor 302. Porous semiconductor portion 302 may be, for instance, a silicon wafer. In some embodiments, pores 304 are cylindrical. In other embodiments, pores 304 may be other shapes including, but not limited to, ellipsoidal, hexagonal, and/or octagonal. Channels or pores 304 may be formed in regular and/or irregular arrays.

In the embodiments depicted in FIG. 6B, pores 304 are separated by about 100 μm in two directions (for instance, vertically and horizontally), and the pore diameter is about 70 μm. Junction region 412 formed by a p-n junction extends to about an 80 μm diameter. Layer 306 of radioactive material (radioactive polymer) 422 adheres to walls of one or more channels or pores 304. In some embodiments, radioactive material (radioactive polymer) 422, may be coupled to and/or removed from one or more selected channels or pores 304 randomly or with a given pattern, as shown in FIG. 6B. In some embodiments, layer 306 is of a thickness ranging from about 30 nm to about 50 nm.

In still further embodiments of the invention, other tritiated material) e.g., a deuterated polymer, a tritiated polymer with a higher wt % of tritium) and/or other semiconductors (e.g., germanium, silicon-germanium composite, or gallium arsenide) and/or other materials capable of forming appropriate junction regions can be employed. Other methods of forming pores and channels, and other pore and channel shapes and patterns, are used in still further embodiments. Actual dopants of the semiconductor, and related methods of doping, also vary in other embodiments, and are not limited to those recited above.

Beta-voltaic cells may be used advantageously for applications requiring low power and/or long life (e.g., 12 years to over 100 years, depending on energy source). Beta-voltaic cells will operate in extreme environments, ranging from −100° C. to +150° C. and are shock tolerant. The size of a beta-voltaic cell may range from a button battery size to "D" cell size. Cells may be formed into arrays to increase battery size. Substantially all emissions in a beta-voltaic cell are captured within the three-dimensional diode matrix, substantially eliminating harmful radiation, leaching, contamination, and other negative environmental impact. Beta-voltaic cells are highly efficient and may be may be manufactured by semiconductor techniques known in the art.

Beta-voltaic cells may be used as stand-along power sources or as trickle-chargers to increase the utility and practical life of chemical batteries. Applications for beta-voltaic cells include, but are not limited to: outer space (space vehicles, satellites, etc.), subsea (valves, actuators, sensors, controls, telemetry, etc.), subsurface (real-time measurements, four-dimensional seismic measurements, etc.), microelectronics (microelectronic mechanical systems, etc.), communications (RFID tags, implanted microcircuits, etc.), government and military (covert operations, sensors, detectors, etc.), medical (pacemakers, defibrillators, microstimulators, neurostimulators, cochlear implants, etc.).

In this patent, certain U.S. patents, U.S. patent applications, and other materials (e.g., articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A process comprising:
   (a) selecting a liquid polymer, wherein the liquid polymer is selected from the group consisting of poly(vinylacetylene), TMS poly(vinylacetylene), and poly(vinyldiacetylene); and
   (b) tritiating the liquid polymer to yield a tritiated liquid polymer, wherein
      (i) the tritiated liquid polymer has a ratio of tritium atoms to carbon atoms of at least about 1:1, and
      (ii) the tritiating of the liquid polymer in step (b) comprises a method selected from the group consisting of addition, substitution, and combinations thereof.

2. The process of claim 1, wherein the amount of tritium in the tritiated liquid polymer is at least about 20 wt %.

3. The process of claim 1, wherein the tritiated liquid polymer is $[C_4H_3T_5]_n$.

4. The process of claim 1, wherein the tritiated liquid polymer is tritiated poly(1-ethylethylene).

5. The process of claim 1, wherein the tritiated liquid polymer is saturated.

6. The process of claim 1, wherein the step of tritiating the liquid polymer comprises addition.

7. The process of claim 1, wherein the step of tritiating the liquid polymer comprises catalytic tritium addition.

8. The process of claim 1, wherein the liquid polymer has at least one carbon-carbon triple bond, and wherein the step of tritiating the liquid polymer comprises addition of the tritium in the form of tritium gas to the carbon-carbon triple bond.

9. The process of claim 1, wherein the liquid polymer has at least one carbon-carbon double bond, and wherein the step of tritiating the liquid polymer comprises addition of the tritium in the form of tritium gas to the carbon-carbon double bond.

10. The process of claim 1, wherein the step of tritiating the liquid polymer comprises substitution.

11. The process of claim 1, wherein the step of tritiating the liquid polymer comprises $T_2O$ hydrolysis.

12. The process of claim 1, wherein the step of tritiating the liquid polymer comprises addition and substitution.

13. The process of claim 1, wherein the ratio of tritium atoms to carbon atoms in the tritiated liquid polymer is at least about 1.25:1.

14. The process of claim 1, wherein the ratio of tritium atoms to carbon atoms in the tritiated liquid polymer is at least about 1.5:1.

15. The process of claim 1, wherein the ratio of tritium atoms to carbon atoms in the tritiated liquid polymer is at least about 2:1.

16. The process of claim 1, further comprising synthesizing the liquid polymer, wherein the liquid polymer is synthesized from two or more compounds, wherein at least one of said compounds is vinyl bromide.

17. The process of claim 16, wherein the synthesizing of the liquid polymer comprises reacting vinyl bromide with trimethylsilylacetylene ((TMS) acetylene).

18. The process of claim 16, wherein the vinyl bromide is tritiated before the synthesizing of the liquid polymer.

19. The process of claim 1, wherein the selecting of the liquid polymer in step (a) comprises selecting a liquid polymer comprising tritium atoms and wherein the tritiating of the liquid polymer in step (b) further tritiates the liquid polymer selected in step (a).

* * * * *